(12) United States Patent
Biedermann et al.

(10) Patent No.: US 12,396,864 B2
(45) Date of Patent: Aug. 26, 2025

(54) IMPLANT FOR ENGAGEMENT BETWEEN VERTEBRAE, AND IMPLANT KIT

(71) Applicant: BIEDERMANN TECHNOLOGIES GMBH & CO. KG, Donaueschingen (DE)

(72) Inventors: Timo Biedermann, Trossingen (DE); Berthold Dannecker, St. Georgen (DE); Lutz Biedermann, VS-Vilingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 18/733,267

(22) Filed: Jun. 4, 2024

(65) Prior Publication Data

US 2024/0407926 A1    Dec. 12, 2024

Related U.S. Application Data

(60) Provisional application No. 63/506,735, filed on Jun. 7, 2023.

(51) Int. Cl.
*A61F 2/44* (2006.01)
*A61F 2/30* (2006.01)

(52) U.S. Cl.
CPC .... *A61F 2/442* (2013.01); *A61F 2002/30138* (2013.01); *A61F 2002/30235* (2013.01);
(Continued)

(58) Field of Classification Search
CPC ............ A61F 2/442; A61F 2002/30138; A61F 2002/30235; A61F 2002/30331;
(Continued)

(56) References Cited

U.S. PATENT DOCUMENTS 5,571,192 A * 11/1996 Schonhoffer ............. A61F 2/44
606/907
5,702,451 A    12/1997 Biedermann et al.
(Continued)

FOREIGN PATENT DOCUMENTS

EP    1 800 627 A2    6/2007
EP    2 108 340 A1    10/2009
(Continued)

OTHER PUBLICATIONS

Extended European Search Report for Application No. 23177921.6, dated Jan. 4, 2024, 13 pages.

*Primary Examiner* — Jessica Weiss
(74) *Attorney, Agent, or Firm* — Womble Bond Dickinson (US) LLP (57) ABSTRACT

An implant that is implantable between vertebrae includes a monolithic body with a first end and a second end opposite the first end, an outer surface extending axially from the first end to the second end, a plurality of teeth at the first end, each of the teeth extending axially away from the second end to a free end, and an abutment surface facing away from the second end that is positioned radially inwardly relative to at least one of the teeth. The abutment surface is recessed axially relative to the free ends of the teeth to an extent such that the abutment surface is configured to contact a vertebra when the implant is implanted. The monolithic body is configured to extend axially over a majority of an entire axial length of the implant.

19 Claims, 11 Drawing Sheets

(52) U.S. Cl.
CPC ............... *A61F 2002/30331* (2013.01); *A61F 2002/3055* (2013.01); *A61F 2002/30561* (2013.01); *A61F 2002/30892* (2013.01); *A61F 2002/3092* (2013.01)

(58) Field of Classification Search
CPC .... A61F 2002/3055; A61F 2002/30561; A61F 2002/30892; A61F 2002/3092
USPC .......................................... 623/17.11–17.16
See application file for complete search history.

(56) References Cited

U.S. PATENT DOCUMENTS

| | | | |
|---|---|---|---|
| 5,702,455 A * | 12/1997 | Saggar | A61F 2/44 623/17.15 |
| 5,709,683 A * | 1/1998 | Bagby | A61F 2/44 623/17.11 |
| 5,897,556 A * | 4/1999 | Drewry | A61B 17/8085 606/247 |
| 6,086,613 A * | 7/2000 | Camino | A61F 2/4465 623/17.16 |
| 6,200,348 B1 | 3/2001 | Biedermann et al. | |
| 6,616,695 B1 * | 9/2003 | Crozet | A61F 2/4465 606/279 |
| 6,776,798 B2 * | 8/2004 | Camino | A61F 2/442 623/17.16 |
| 6,866,682 B1 * | 3/2005 | An | A61F 2/44 623/17.11 |
| 7,547,325 B2 | 6/2009 | Biedermann et al. | |
| 7,837,735 B2 * | 11/2010 | Malone | A61B 17/864 623/17.16 |
| 8,187,331 B2 * | 5/2012 | Strohkirch, Jr. | A61F 2/4611 623/17.11 |
| 8,231,681 B2 * | 7/2012 | Castleman | A61F 2/44 623/17.16 |
| 8,241,363 B2 * | 8/2012 | Sommerich | A61F 2/4611 606/57 |
| 8,252,054 B2 * | 8/2012 | Greenhalgh | A61F 2/44 623/17.11 |
| 8,328,871 B2 * | 12/2012 | Capote | A61F 2/44 623/17.16 |
| 8,372,151 B2 * | 2/2013 | Hsu | A61F 2/44 623/17.11 |
| 8,568,482 B2 * | 10/2013 | Kraus | A61F 2/4611 623/17.15 |
| 8,657,882 B2 * | 2/2014 | Bonin, Jr. | A61F 2/44 623/17.11 |
| 8,771,357 B2 * | 7/2014 | Biedermann | A61F 2/4465 623/17.11 |
| 9,254,199 B2 * | 2/2016 | Biedermann | G02F 1/13439 |
| 9,283,086 B2 * | 3/2016 | Hirschl | A61F 2/4455 |
| 10,278,833 B2 | 5/2019 | Howard et al. | |
| 2003/0191531 A1 * | 10/2003 | Berry | A61F 2/4455 623/17.11 |
| 2005/0267471 A1 * | 12/2005 | Biedermann | A61F 2/44 606/907 |
| 2009/0112324 A1 * | 4/2009 | Refai | A61F 2/44 623/17.11 |
| 2009/0138083 A1 * | 5/2009 | Biyani | A61F 2/44 623/17.11 |
| 2011/0045087 A1 * | 2/2011 | Kerr | A61L 27/56 424/490 |
| 2012/0130493 A1 | 5/2012 | McLaughlin et al. | |
| 2013/0338775 A1 * | 12/2013 | Biedermann | G02F 1/13458 623/17.16 |
| 2015/0230938 A1 * | 8/2015 | Biedermann | A61B 17/8023 623/17.16 |
| 2021/0059835 A1 | 3/2021 | Howard | |
| 2023/0134792 A1 * | 5/2023 | Berry | A61F 2/4455 623/17.16 |
| 2023/0255787 A1 * | 8/2023 | Howard | A61F 2/4455 623/17.16 |

FOREIGN PATENT DOCUMENTS

| | | |
|---|---|---|
| WO | WO 99/32055 A1 | 7/1999 |
| WO | WO 2005/070346 A1 | 8/2005 |

* cited by examiner

IMPLANT FOR ENGAGEMENT BETWEEN VERTEBRAE, AND IMPLANT KIT

CROSS-REFERENCE TO RELATED APPLICATION(S)

The present application claims priority to and the benefit of U.S. Provisional Patent Application No. 63/506,735, filed Jun. 7, 2023, the contents of which are hereby incorporated by reference in their entirety, and claims priority from European Patent Application EP 23 177 921.6, filed Jun. 7, 2023, the contents of which are hereby incorporated by reference in their entirety.

BACKGROUND

Field

The application relates to an implant for engagement between vertebrae, and to an implant kit including such an implant. In particular, the application relates to an implant of the spacer type to be inserted between vertebrae.

Description of Related Art

A space holder, in particular for a vertebra for an intervertebral disc, is known from U.S. Pat. No. 5,702,451. The space holder includes a jacket having apertures and first and second edges. The edges have circumferentially adjacent recesses each extending in a direction towards the other edge, and a stop provided at at least one of the edges, the stop being spaced from the outer edge. The stop is formed by a member having an outer contour corresponding to the inner contour of a jacket and nose-like projections for engaging the recesses. The jacket may be cut to length.

U.S. Pat. No. 7,547,325 B2 describes a space keeper for insertion between two vertebrae which has a variable axial length. The space keeper possesses a sleeve-like first member and a second member guided in the first member and movable relative to the first member in the axial direction for adjusting an overall length.

SUMMARY

The above described types of space holders or keepers, also known as spacers, may be used for various purposes, such as a spacer for one or more vertebrae that have been removed or as a spacer for an intervertebral disc. Due to the various possible clinical applications, patient specific conditions and different locations on the spinal column where such spacers are to be used, usually a large inventory of spacers of different sizes and with different characteristics is required to select an appropriate implant.

It is therefore an object of the invention to provide an implant for engagement between vertebrae, and an implant kit that allows for a reduction of the inventory of implants to be provided for surgery.

According to an aspect of an embodiment of the invention, an implant for engagement between vertebrae includes a monolithic body having a first edge at a first end and a second edge at a second end opposite to the first end, an outer surface extending between the first edge and the second edge, the body defining a central axis extending through the first end and the second end, a plurality of teeth forming the first edge, and an abutment surface provided at a distance from the first edge and extending substantially transverse to the teeth, preferably in a direction towards the central axis. The abutment surface is configured to engage a portion of a vertebra or an endplate that serves for engagement with a vertebra. In a further development, a plurality of intermediate abutment surfaces are provided axially along the length of the body.

The implant may be easily cut to a desired length. Hence, an implant with a desired length can be made available prior to surgery, to adapt the implant to the size of the intervertebral space where the implant is intended to be placed. Optionally, the implant can be combined at one or at both ends, for example, after cutting the implant, with a suitable end plate that is configured to engage a vertebra. Such an end plate may have appropriate characteristics, such as a specific size, an engagement structure, or a lordotic angle. Preferably, the end plates at both ends can be detachably connected with the implant body.

The mesh structure of the implant may facilitate ingrowth of tissues and vessels.

According to a further aspect of an embodiment of the invention, the implant is a length adjustable implant that includes a first tubular member and a second tubular member movably positionable in the first tubular member, and a length adjustment structure to adjust the axial position of the second tubular member relative to the first tubular member. At least the second tubular member is a monolithic body having a first edge at a first end and a second edge at a second end opposite to the first end, an outer surface extending between the first edge and the second edge, the body defining a central axis extending through the first end and the second end, a plurality of teeth forming the first edge, and an abutment surface provided at a distance from the first edge and extending substantially transverse to the teeth towards the central axis.

With a length-adjustable implant according to embodiments of the invention, the length of the implant can be adjusted in small steps or in a quasi-stepless manner. End plates can be selected according to the requirements of the actual clinical application. In a further development, the second tubular member may also be cut to length, so that even more variability is provided.

The length adjustment structure permits locking of the position of the second tubular member relative to the first tubular member using friction between engaged inclined surfaces. Hence, the axial position can be easily fixed and released with an instrument.

Moreover, according to another aspect of an embodiment of the invention, a kit is provided that includes a first implant that is configured to be cut to length and a second implant, the length of which is, preferably reversibly, adjustable, and optionally an endplate that is configured to be detachably mountable to the first implant or to the second implant. Further end plates for various purposes may also be provided.

Thus, a kit according to embodiments of the invention provides a modular system that is configured to provide a multitude of implants with different properties, while only including a few parts. This contributes to cost-saving in hospitals.

According to a further aspect of embodiments of the invention, the implant is manufactured with an additive manufacturing technique, such as laser sintering, laser melting, electron beam melting, fused deposition molding (FDM), or other similar methods. With such techniques, any three-dimensional shape from CAD-data can be manufactured, especially any complicated shapes that previously could not or could only be manufactured with subtractive methods. The manufacturing can be carried out on demand for a specific patient's application.

BRIEF DESCRIPTION OF THE DRAWINGS

Further features and advantages will become apparent from the description of embodiments by means of the accompanying drawings. In the drawings.

DETAILED DESCRIPTION

Referring to FIGS. 1 to 8, an implant 1 according to a first embodiment includes a monolithic implant body 10 and optionally a first end plate 20 and/or a second end plate 30. The implant body 10 may be formed as a tubular mesh. The implant body 10 has a first end 10a and an opposite second end 10b, and defines a central axis L that extends through the first end 10a and the second end 10b. In the embodiment shown, the central axis L is also a longitudinal axis of the elongate body. An outer envelope of the implant body 10 may be cylindrical, oval, or kidney-shaped, or may have any other shape that is suitable to be placed between vertebrae. The mesh defines apertures 2 that extend between an outer surface 3a and an inner surface 3b (FIG. 8) and that are spaced apart from one another at regular intervals in a circumferential direction. The apertures 2 may be diamond-shaped and may have a longitudinal diagonal that extends parallel to the central axis L of the implant body 10. Each aperture 2 is mirror-symmetrical to the longitudinal diagonal of the diamond. Adjacent rows 2a, 2b of apertures 2 in the axial direction may be mutually offset by half of the axial height of the apertures 2. In this manner, a grid is formed having webs or segments 4a, 4b intersecting at an acute angle and forming equal angles with the longitudinal diagonal of the apertures 2. In the circumferential direction, there may be an equal number of apertures 2 in each row. The sizes of the apertures 2 and of the webs 4a, 4b are such that, in one row, there is an integer or whole number of apertures 2.

The webs 4a, 4b form a first edge 5a at the first end and a second edge 5b at the second end 10b. By means of the intersecting webs 4a, 4b, the edge 5a forms teeth 6 that are arranged in a ring around the central axis L. The free ends of the teeth 6 may be located in a plane perpendicular to the central axis L. Hence, the free ends of the teeth 6 form the first end 10a and the second end 10b of the body, respectively. It shall be noted that the ring of teeth 6 in the embodiment shown is circular, since the body 10 has a cylindrical outer shape. The ring may, however, have any other shape adapted to the outer shape of the body. In a modified embodiment, the free ends of the teeth may be arranged in a plane that is angled relative to the longitudinal axis L of the body.

At a distance from the first end 10a, a first abutment surface 7a or a stop is formed. The first abutment surface 7a serves as a support for the end plate 20 to be connected to the implant body at the first end 10a. In greater detail, the first abutment surface 7a extends in a plane substantially perpendicular to the central axis L and may be substantially flat. The teeth 6 project out of the first abutment surface 7a in the axial direction. The first abutment surface 7a includes a plurality of radially extending webs or segments 8 that extend from an inner coaxial ring 9 to the teeth 6. A width of the webs 8 may increase as the webs extend radially outwardly from the inner ring 9. The webs 8 are arranged in an alternating manner with respect to the teeth 6, or in other words, a radially outer end of the webs 8 ends at the inner surface 3b in a gap between consecutive teeth 6. Hence, the number of webs 8 corresponds to the number of apertures 2 in the circumferential direction. In the circumferential direction, there are also gaps 8a between the webs 8. The ring 9 and the webs 8 have a certain thickness in the axial direction, that may be about a quarter of the height of the apertures 2.

Figure 1:
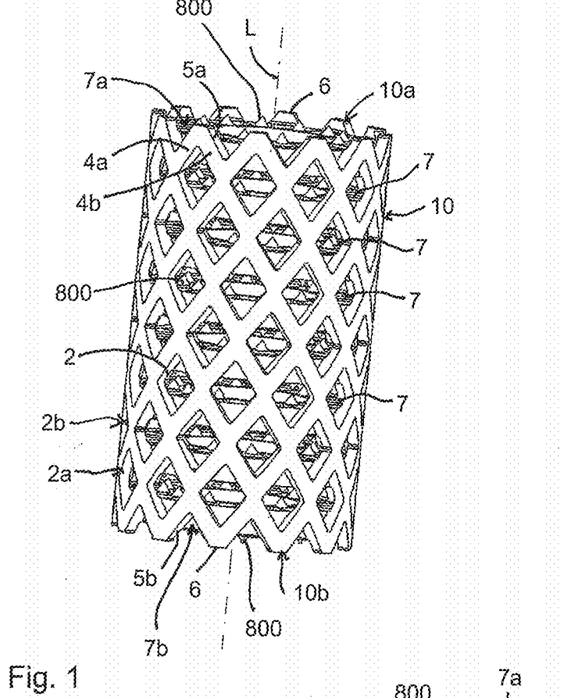
FIG. 1 shows a perspective view of an implant according to a first embodiment.
Figure 5:
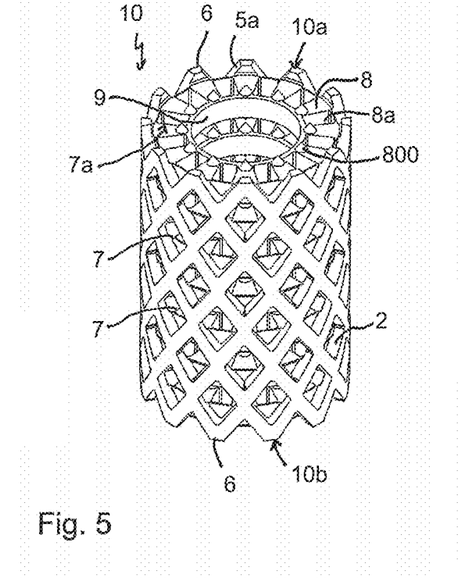
FIG. 5 shows a perspective view from a top of the implant of FIG. 1.
Figure 6:
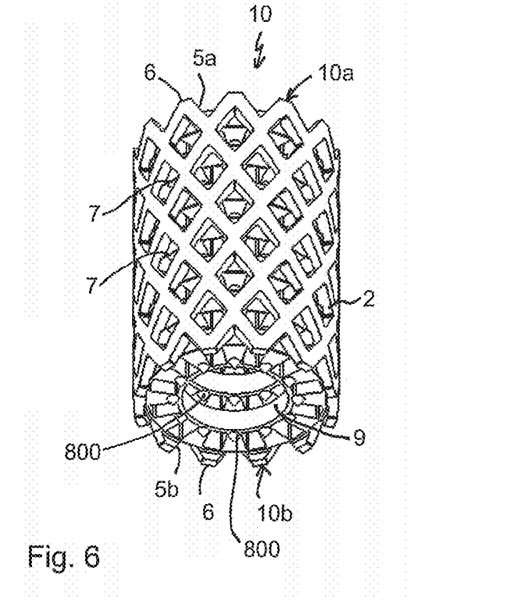
FIG. 6 shows a perspective view from a bottom of the implant of FIGS. 1 and 5.
Figure 7:
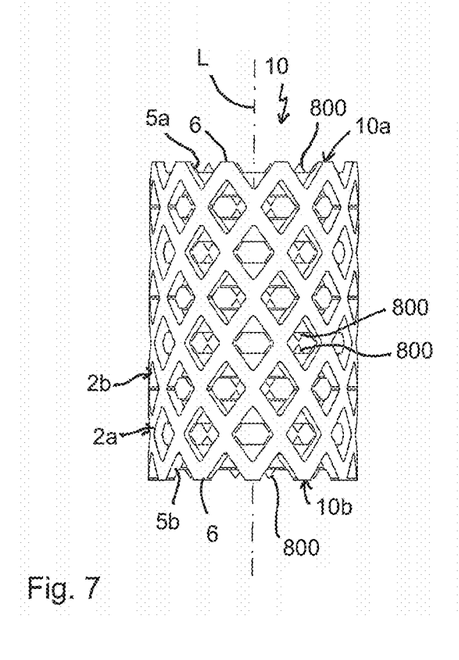
FIG. 7 shows a side view of the implant of FIGS. 1, 5, and 6.
Figure 8:
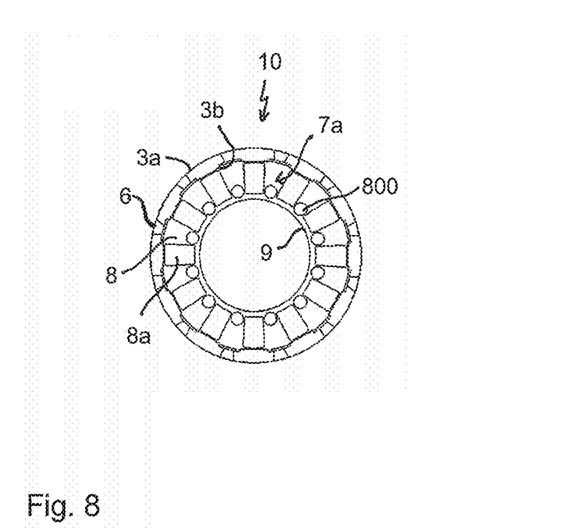
FIG. 8 shows a top view of the implant of FIGS. 1 and 5 to 7.
Figure 9:
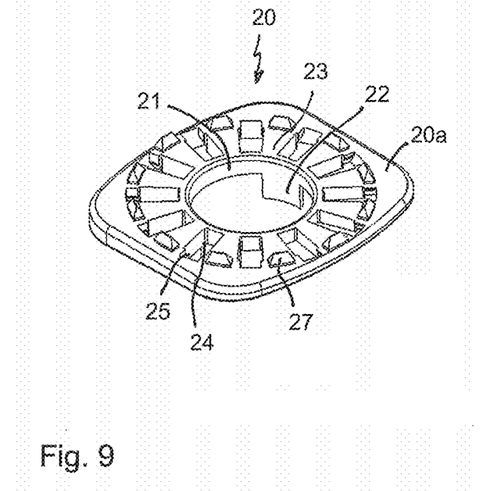
FIG. 9 shows a perspective view from a top of a first end plate of the implant of FIGS. 3 and 4 that is configured to be connected to a first end of the implant.
Figure 10:
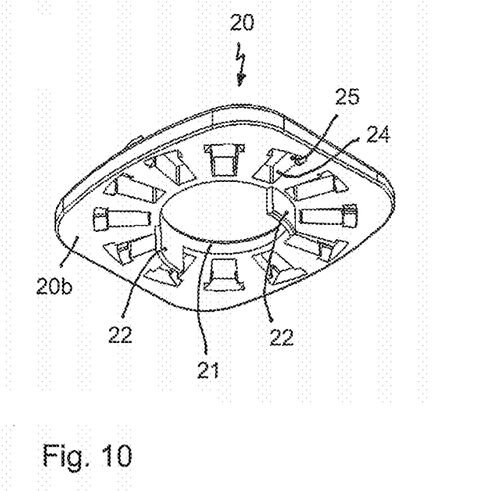
FIG. 10 shows a perspective view from a bottom of the end plate of FIG. 9.

Lastly, on each web 8 adjacent to the ring 9, there are spikes 800 in both axial directions, i.e., pointing toward the first end 10a and toward the second end 10b. The height of the spikes 800 may be smaller than the height of the teeth 6.

At the second end 10b, there is a second abutment surface 7b that is identical to the first abutment surface 7a and that is provided at a distance from the free ends of the teeth 6.

Figure 2:
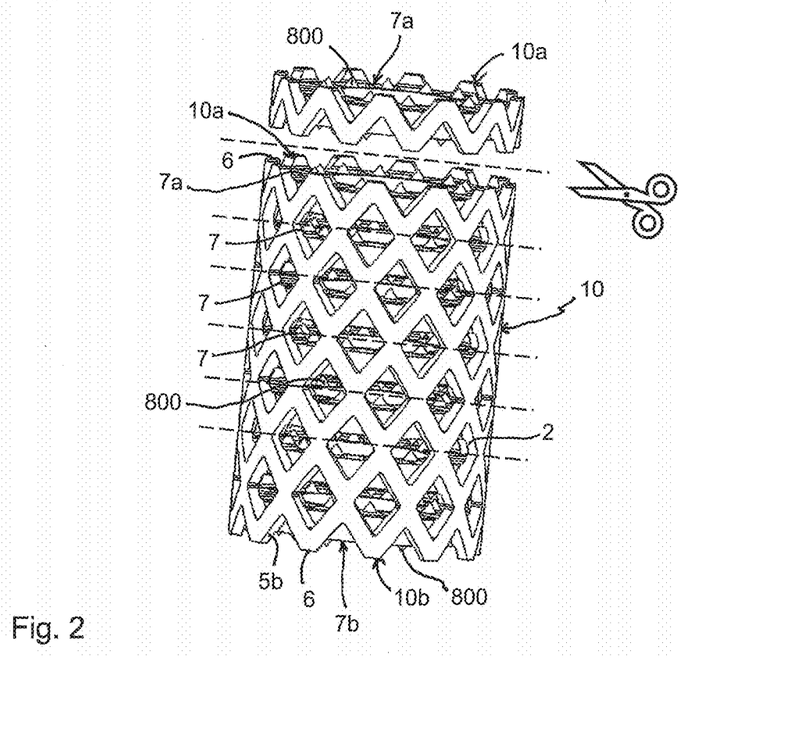
FIG. 2 shows a perspective view of the implant of FIG. 1, cut to a desired length and showing further cutting options.

A plurality of intermediate abutment surfaces 7 are formed that are identical to the first abutment surface 7a and to the second abutment surface 7b at equidistant axial positions within the body 10, preferably at distances of half of the axial height of a row of the mesh structure. In greater detail, the further abutment surfaces 7 are provided at positions such that by cutting the implant body 10 to a desired length in a plane perpendicular to the central axis L and at the center of a row of the apertures 2 in the axial direction, an implant body is provided that is shortened by a multiple of a half of the axial length of one mesh row, or by a multiple of a half of the height of the apertures 2. Thereby a cutting segment is defined, as shown in FIG. 2. Each of the intermediate abutment surfaces 7 may form, after cutting, a first abutment surface 7a or, if the implant body is shortened from the second end 10b, a second abutment surface 7b. Moreover, the implant body has the same shape if it is turned upside down. Before cutting, the position of the teeth 6 is offset in a circumferential direction from the position of the teeth 6 of the adjacent segment.

With the structure of the abutment surfaces 7a, 7, 7b, longitudinal channels are formed by the gaps 8a between the webs 8, as well as circumferential channels between the rings 9. This may enhance the stability of the implant body 10.

The implant body 10 is preferably manufactured using an additive manufacturing method. In an additive manufacturing method, the implant body is built up layer-by-layer based on three-dimensional data that characterize the shape and the size of the implant body. As an example, a powder bed based layer manufacturing technique, such as selective laser-melting (SLM), includes the steps of applying a layer of a building material, such as a powder, in particular a metal powder or a plastic powder, onto a support surface, and selectively solidifying or melting the powder at positions corresponding to the cross-section of the implant body in the respective layer. Subsequently, the steps of applying and melting further layers of the implant body are repeated until the implant body is finished. The data of the cross-section of the implant body in the respective layer and the data for controlling the layer manufacturing apparatus results from CAD or CAM data of the implant body and corresponding slice data. In particular, undercuts and complex shapes can be built-up. The manufactured implant body may show characteristics of the manufacturing process, such as a slightly rough surface or the traces of the laser in a finely prepared cut-out portion. Thereby the manufacturing process may be identified. Other additive manufacturing processes, such as electron beam-melting, FDM (fused deposition molding), and others may also be contemplated.

Figure 11:
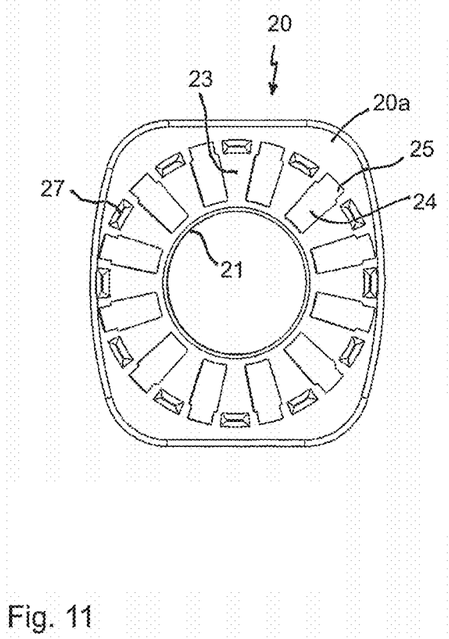
FIG. 11 shows a top view of the end plate of FIGS. 9 and 10.
Figure 12:
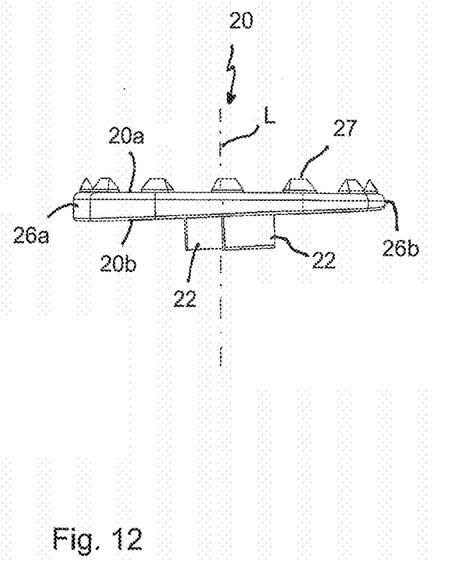
FIG. 12 shows a side view of the end plate of FIGS. 9 to 11.

Referring further to FIGS. 9 to 12, the first end plate 20 or top end plate is configured to be connected to the first end 10a of the implant body 10. The first end plate 20 is a substantially flat, tubular, plate-shaped member with an outer surface 20a that is configured to engage a vertebra, in particular a vertebral body, and an opposite inner surface 20b that is configured engage the implant body 10. An outer contour of the end plate 20 may be, as shown in FIG. 11, in a top view substantially quadrangular with a width greater than a maximum outer width of the implant body 10. However, the shape of the end plate 10 can be any shape and/or size that is suitable for engagement with a vertebra. The inner surface of the tube of the end plate 20 forms a ring 21 that may have a slightly smaller diameter than the ring 9 of the implant body. Projections 22 extend from the ring 21 in the axial direction. The projections may be offset by 180° and are configured to slide along the inner surface of the ring 9 of the implant body 10. The projections 22 may have a shape of a portion of a cylindrical wall. The projections 22 may serve for centering the end plate 20 when mounting the end plate 20 to the implant body 10. A plurality of radially extending webs or segments 23 are provided that extend from the ring 21 radially outward. Between the webs 23, gaps 24 or openings are formed that serve for receiving the end portions of the teeth 6 of the implant body 10. Thus, the number of webs 23 corresponds to the number of teeth 6 of the implant body. Each gap 24 has a radially outer end portion 25 corresponding to the position of the teeth 6. In greater detail, the shape of the end portions 25 may be adapted to the shape of the end portions of the teeth 6, so that the teeth can be received in a form-fit manner therein. In particular, side walls of the end portion 25 may be inclined at an angle at which the webs 4a, 4b of the mesh intersect.

Figures 3, 4:
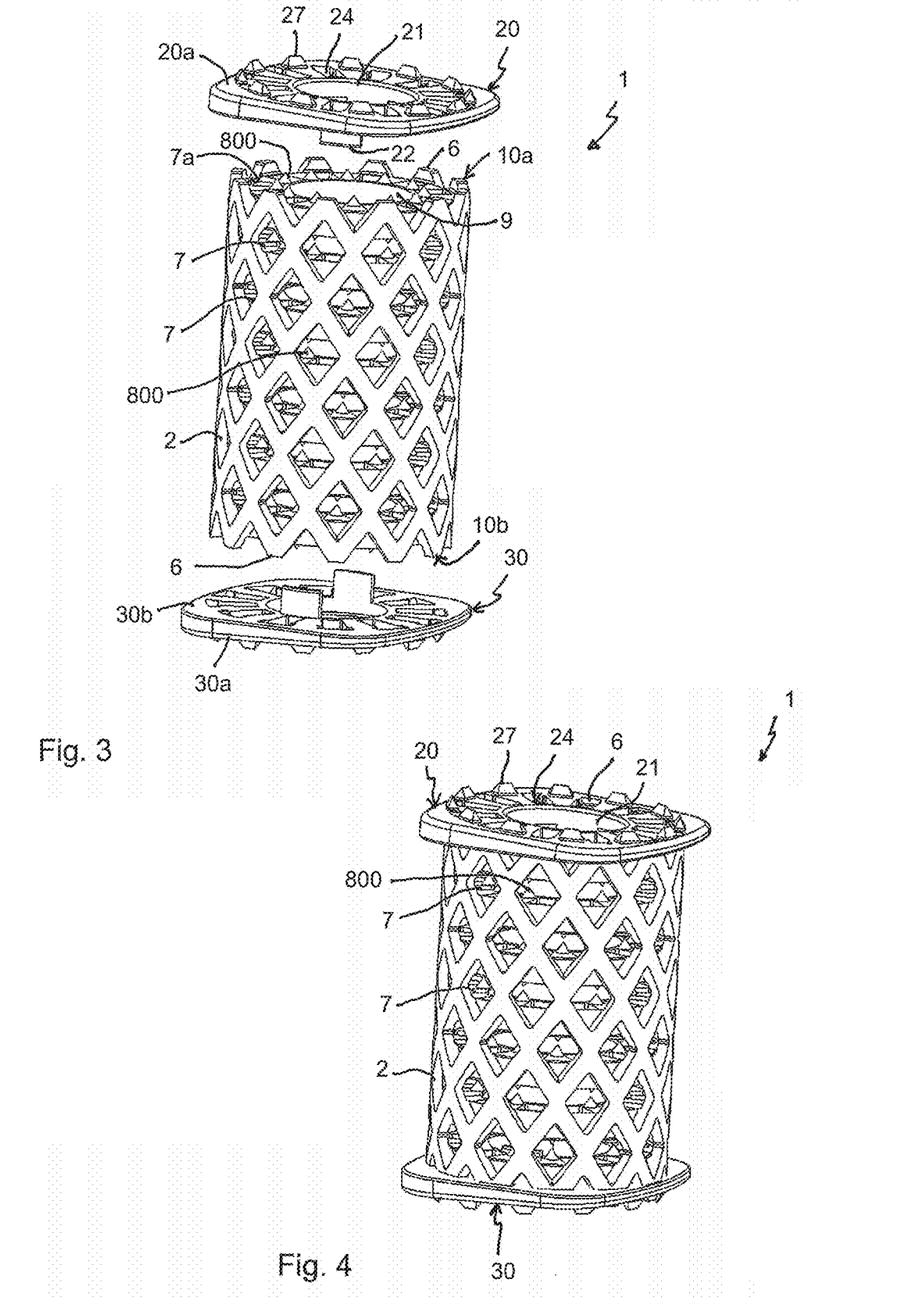
FIG. 3 shows a perspective exploded view of the implant of either FIG. 1 or 2 with end plates that can be detachably mounted to the implant.
FIG. 4 shows the implant of FIG. 3 in an assembled state.

When the end plate 20 is mounted to the first end 10a of the implant body 10, the webs 23 of the end plate 20 abut against the webs 8 that form the first abutment surface 7a of the implant body 10. In embodiments with spikes 800, the webs 23 of the end plate 20 may abut against the spikes 800, which can be considered part of or extensions of the webs 8. The projections 22 abut in a radial direction against the inner surface of the ring 9 of the implant body 10. The teeth 6 extend into the end portions 25 of the gaps 24 between the webs 23.

The first end plate 20 may have a wedge shape to provide a lordotic angle. As can be seen in particular in FIG. 12, the end plate 20 is thicker at a first side 26a relative to the central axis L compared to the opposite side 26b. Various end plates 20 with different angles may be provided to generate a modular system. Moreover, on the outer surface 20a, at a radially outer portion of the webs 23, and either radially outwardly from or at substantially a same radial distance from the central axis as the end portions 25 of the gaps 24, spikes 27 may be provided, respectively, that form a ring around the central axis L. The spikes 27 may serve for engagement with the vertebra. The spikes may have approximately the same width or may have a slightly smaller width than at least part of the webs 23.

Turning now to FIGS. 13 to 16, the second end plate 30 or bottom end plate is also a substantially flat, tubular plate member with an outer surface 30a that is configured to engage a vertebra and an opposite inner surface 30b that is configured to be connected to the implant body 10. The outer contour of the second end plate 30 may be the same as or may be different from the outer contour of the first end plate 20.

The second end plate 30 includes an inner ring 31. Two projections 32 that are located preferably opposite to each other project from the inner surface 30b such that they can engage and slide along the inner ring 9 of the second abutment surface 7b at the second end 10b of the implant body 10. Hence, the inner surface of the inner ring 32 has a somewhat smaller inner diameter compared to the inner diameter of the ring 9. A plurality of webs or segments 33 extend radially outward from the inner ring 32. The width of the webs 33 in the circumferential direction may be smaller adjacent to the inner ring 32 and increases as the webs extend radially outwardly. The number and position of the webs 33 corresponds to the number and position of the webs 8 at the second abutment surface 7b of the implant body 10. Between the webs 33, gaps 34 or openings are provided, each of which has at its radially outer end a circumferentially broadened portion 35 for receiving the teeth 6 of the second edge 7b of the implant body 10. Opposite sides 35a of the broadened portion 35 may have an inclination that corresponds to the inclination of the teeth 6, such that the end portion of the teeth 6 can be matingly received in the broadened portion 35.

Figure 13:
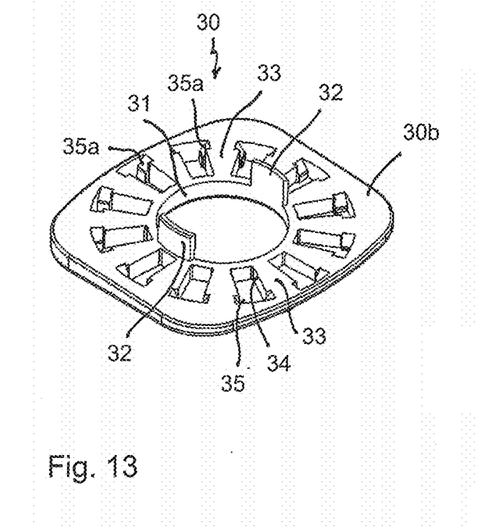
FIG. 13 shows a perspective view from a top of a second end plate of the implant of FIGS. 3 and 4 that is configured to be connected to a second end of the implant.
Figure 14:
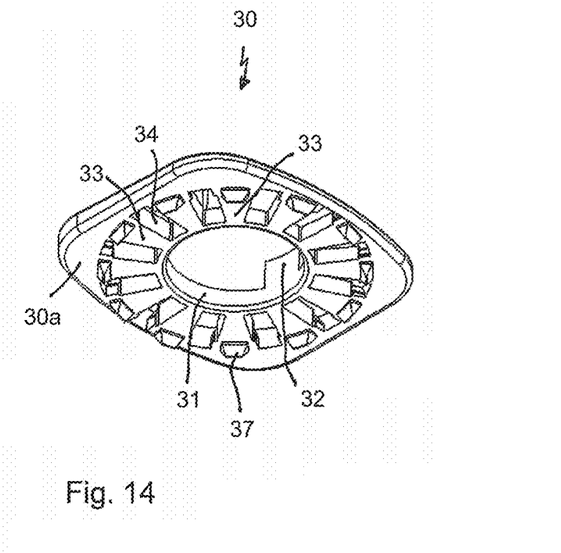
FIG. 14 shows a perspective view from a bottom of the second end plate of FIG. 13.
Figure 15:
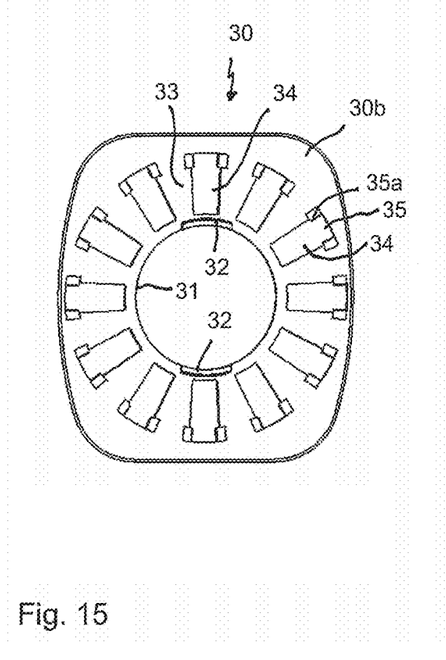
FIG. 15 shows a top view of the second end plate of FIGS. 13 and 14.

On the outer surface 30a at a radially outer position of the webs 33, spikes 37, similar to the spikes 27 of the first end plate 20, are provided that serve for engagement with a vertebra. Hence, the spikes 37 are arranged in a ring and may have a width smaller than the radially outer width of at least part of the webs 33.

Figure 16:
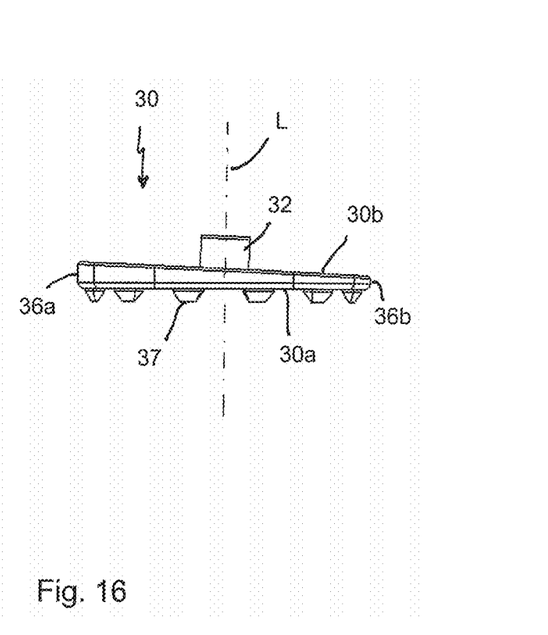
FIG. 16 shows a side view of the second end plate of FIGS. 13 to 15.

As can be seen in particular in FIG. 16, the second end plate 30 may also include a lordotic angle, such that the thickness of the second end plate 30 is greater at one side 36a from the central axis L compared to the opposite side 36b. Different second end plates may be provided with different lordotic angles and/or different sizes and/or different engagement features for engaging vertebra. By means of this, a modular system may be provided that includes one implant body and several first and second end plates that can be combined with the implant body to form an implant for engagement between two vertebral bodies.

Preferably, the first end plate 20 and the second end plate 30 are also manufactured by an additive manufacturing method, similarly as described above.

The implant body, as well as the first end plate and the second end plate, may be made of any bio-compatible material, preferably, however, of titanium or stainless steel, or of any other bio-compatible metal or metal alloy or plastic material. For bio-compatible alloys, a NiTi-alloy, for example Nitinol, may be used. Other materials that can also be used may be magnesium or magnesium alloys. Bio-compatible plastic materials that can be used may be, for example, polyether ether ketone (PEEK) or poly-L-lactide acid (PLLA). The end plates and the implant body may be made of the same material or may be made of different materials.

In use, first, the implant body 10 is used with the length as originally provided and combined with any suitable first end plate 20 and/or second end plate 30. Alternatively, the implant body 10 may be cut to the desired length at the pre-defined positions, so that an implant body that has the same shape but a different length compared to the original implant body is provided. The shortened implant body is then combined with any suitable end plates to provide the implant to be placed between the vertebrae. The end plates 20, 30 are assembled to the first end 10a and the second end 10b of the implant body, respectively. The shortened implant body may have teeth that are offset from the teeth of the cut-away segment, but can be rotated due to its symmetry for connecting with the first end plate 20. The first end plate 20 receives the teeth 6 of the first end 10a in the broadened portions 25. The second end plate 30 receives the teeth 6 of the second end 10b in the broadened portions 35a of the holes 35. Thus, the end plates are rotationally secured with respect to the implant body. When the implant 1 is inserted between two vertebrae, the pressure of the vertebrae onto the end plates keeps the end plates securely fixed to the implant body.

Figures 17, 18:
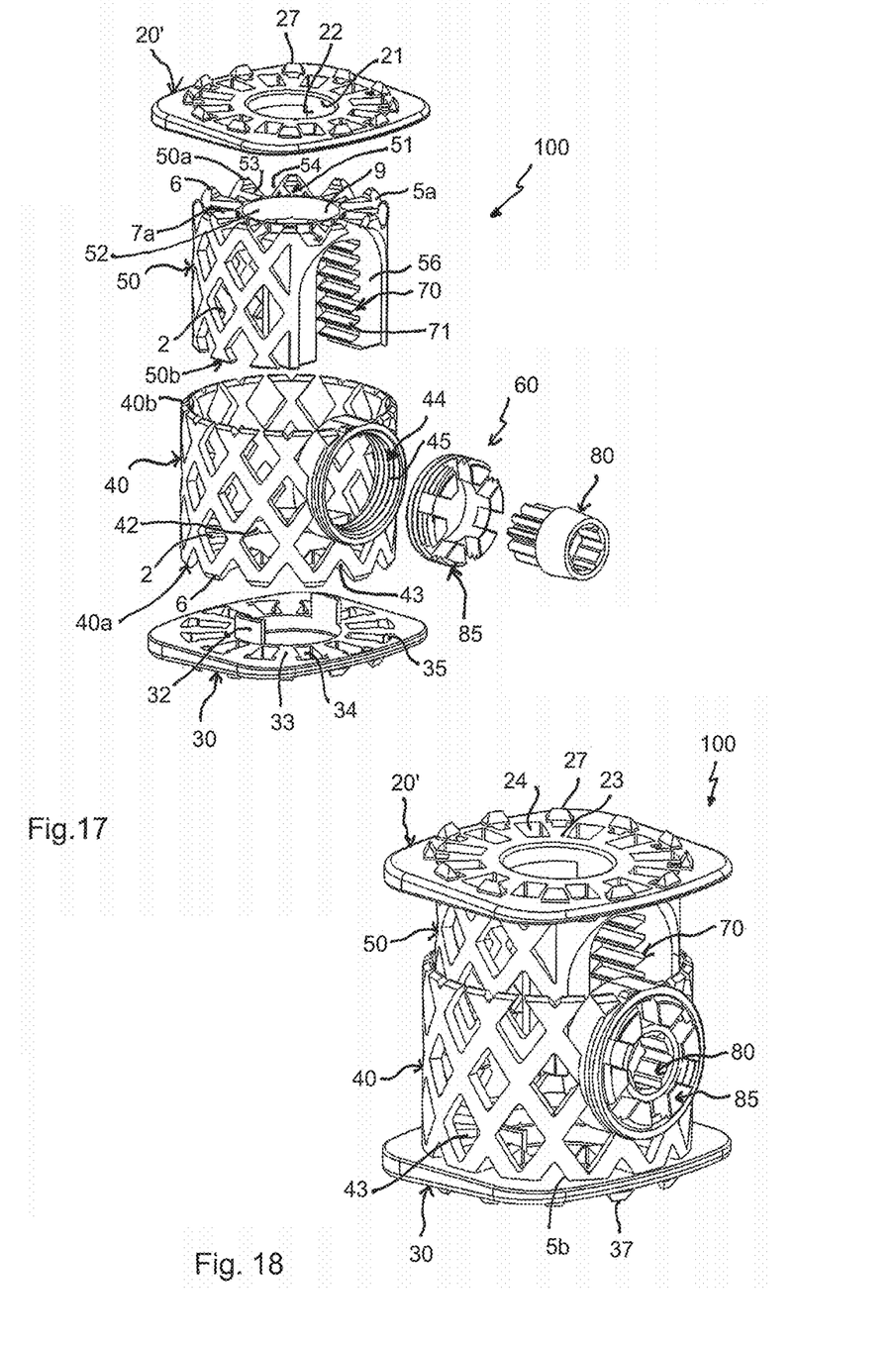
FIG. 17 shows a perspective exploded view of an implant according to a second embodiment.
FIG. 18 shows a perspective view of the implant of FIG. 17 in an assembled state.
Figure 19:
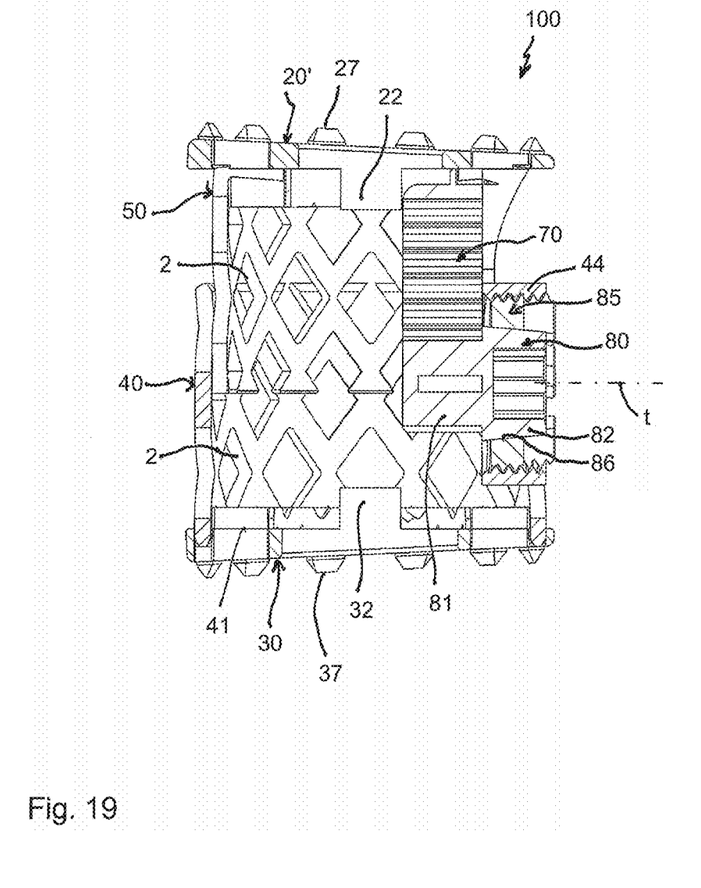
FIG. 19 shows a cross-sectional view of the implant of FIGS. 17 and 18, the cross-section taken in a plane including a longitudinal axis of the implant and extending through a center of a length adjustment mechanism.

As depicted in FIGS. 17 to 19, a second embodiment of an implant 100 for engagement between two vertebrae includes a monolithic first tubular body 40 and a monolithic second tubular body 50 that is positionable in the first tubular body 40 and movable relative thereto in an axial direction. The first tubular body 40 and the second tubular body 50 are connected to each other via a length adjustment structure 60. The length adjustment structure 60 includes an advancement structure 70 provided at the second tubular member 50 and a drive member 80 provided at the first tubular member 40. It shall be noted that the first tubular member 40 and the second tubular member, as well as the portions of the length adjustment structure, are preferably manufactured with an additive manufacturing method similarly as described above. The length adjustment structure can be easily integrated into the monolithic parts. In addition, a locking member 85 is provided that is configured to lock the axial position of the second tubular member 50 relative to the first tubular member 40. The second end plate 30 is the same as for the first embodiment, and is configured to be connected to the first tubular member 40. Additionally, a modified first end plate 20' is provided that is configured to be connected to the second tubular member 50.

As shown in particular in FIGS. 17 and 18, the first tubular member 40 is a mesh cage having a first end 40a, an opposite second end 40b, and a grid or mesh that defines a plurality of apertures 2, preferably diamond-shaped apertures 2. At the second end 40b, the edge includes a plurality of teeth 6. At a distance from the free ends of the teeth 6, an abutment surface 41 is formed that includes an inner ring 42 and a plurality of webs or segments 43 extending in a radial direction from the inner ring 42 to the teeth 6. The webs 43 may have a flat surface on a side that faces the first end 40a, and may have a V-shaped radially extending groove towards the second end 40b, but may also be flat towards the second end 40b. The teeth 6 are configured to be received in the broadened portions 35 of the openings 34 of the second end plate 30. The webs 33 of the second end plate 30 are configured to abut against the webs 43 of the first tubular member 40 when the second end plate 30 is mounted to the first tubular member 40.

In the first tubular member 40 at a position above the second end 40b, a tubular portion 44 is provided, the tube axis t of which is substantially perpendicular to the central axis L. The tubular portion 44 includes an internal thread 45 that is configured to cooperate with the locking member 85. The tubular portion 44 may reach up to the first end 40a.

The second tubular member 50 includes a mesh cage with a first end 50a, an opposite second end 50b, and a mesh or grid that defines a plurality of preferably diamond-shaped apertures 2 similar to the first tubular member 40 and teeth 6 forming the edge at the first end 50a. At a distance from the free ends of the teeth 6 at the first end 50a, a first abutment surface 51 is provided. Similar to the implant body of the first embodiment, the abutment surface 51 includes an inner ring 52 and radially extending webs or segments 53 that are located at positions corresponding to the teeth 6. Between the radially extending webs 53, gaps 54 are provided.

A substantially U-shaped portion 56 extends from the second end 50b up to the gaps between the teeth 6 at the abutment surface 52. The U-shaped portion 56 is open towards the second end 50b. In a direction perpendicular to the central axis L, the U-shaped portion 56 extends into the inner hollow space of the second tubular member 50. At one side of the U-shaped portion 56, an advancement structure 70 is formed that is configured to engage the drive member 80. The advancement structure 70 may be, for example, a ratchet structure or a toothed rack. The teeth 71 of the toothed rack are arranged one after another in the axial direction. When the second tubular member 50 is inserted into the first tubular member 40 and the U-shaped portion 56 is aligned with the tubular portion 44 of the first tubular member 40, the U-shaped portion 56 abuts against the rear side of the tubular portion 44.

As can be seen in FIGS. 20 to 25, the length adjustment structure 60 further includes the drive member 80 and the locking member 85. The drive member 80 includes a pinion portion 81 at its rear side that is configured to be inserted into the first tubular member 40. The pinion portion includes teeth 81a configured to engage the toothed rack of the advancement structure 70 at the second tubular member 50. Adjacent to the pinion portion 81, a conical portion 82 is formed that tapers and narrows as the conical portion extends in a direction away from the pinion portion 81. At the front end of the drive member 80, a recess 83 for engagement with a tool (not shown) for rotating the drive member 80 is formed.

Figures 20, 21, 22, 23, 24, 25:
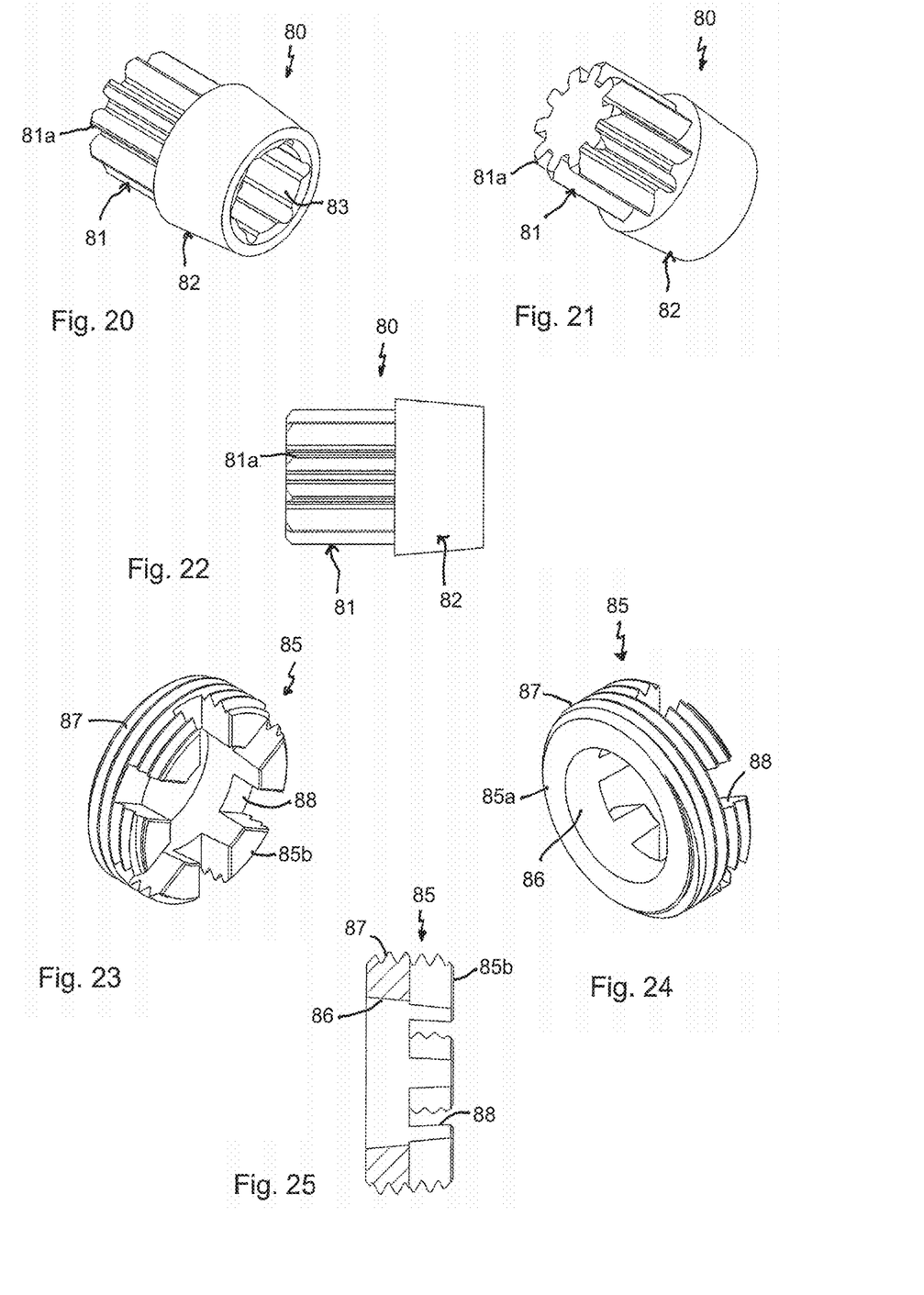
FIG. 20 shows a perspective view from a front of a drive member of the length adjustment mechanism of the implant of FIGS. 17 to 19.
FIG. 21 shows a perspective view from a rear of the drive member of FIG. 20.
FIG. 22 shows a side view of the drive member of FIGS. 20 and 21.
FIG. 23 shows a perspective view from a front of a locking member of the length adjustment mechanism of the implant of FIGS. 17 to 19.
FIG. 24 shows a perspective view from a rear of the locking member of FIG. 23.
FIG. 25 shows a cross-sectional view of the locking member of FIGS. 23 and 24.
Figure 26:
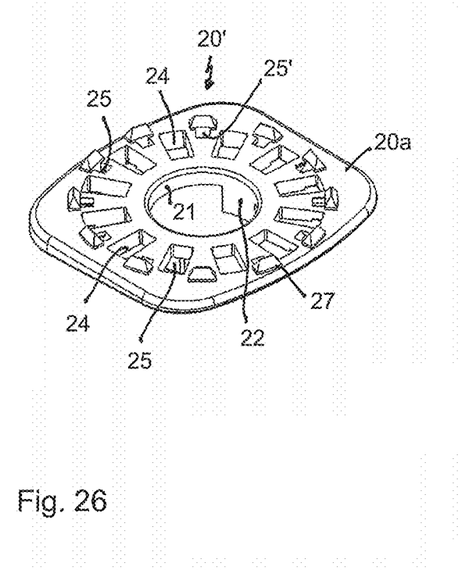
FIG. 26 shows a perspective view from a bottom of an end plate of the implant of FIGS. 17 to 19.
Figure 27:
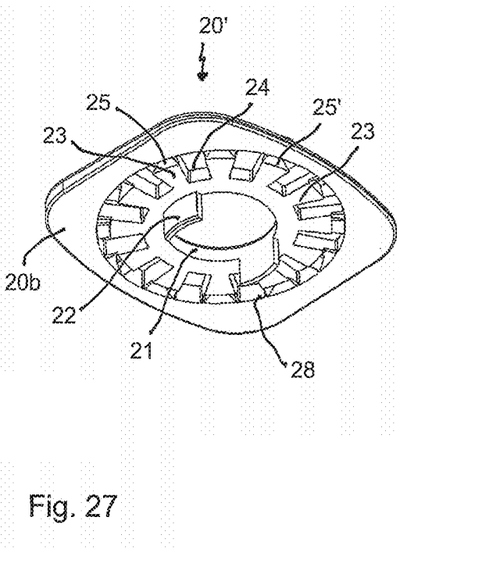
FIG. 27 shows a perspective view from a top of the end plate of FIG. 26.
Figure 28:
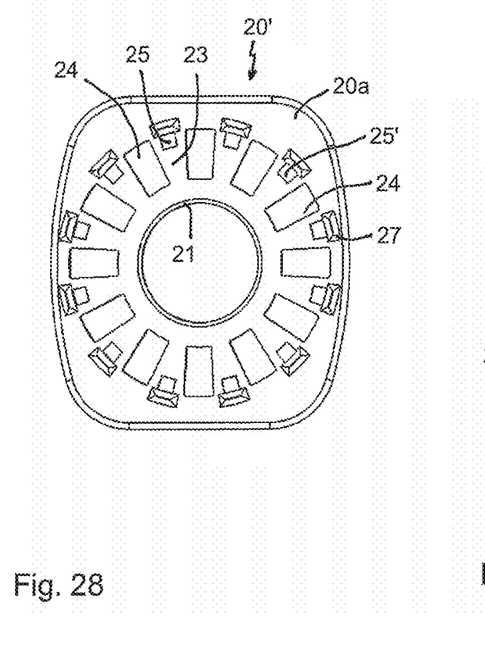
FIG. 28 shows a top view of the end plate of FIGS. 26 and 27
Figure 29:
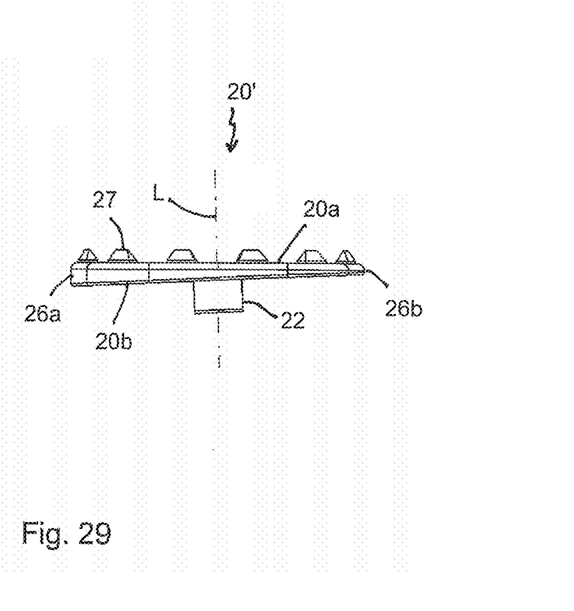
FIG. 29 shows a side view of the end plate of FIGS. 26 to 28.

The locking member 85 is a screw member with an outer thread 87 that is configured to cooperate with the internal thread 45 of the tubular portion 44 of the first tubular member 40. In the assembled state, a rear side 85a of the locking member 85 is oriented towards the second tubular member 50 and a front side 85b of the locking member is oriented towards the outside. Further, the locking member 85 has a conical through-hole 86 that extends coaxially with the screw thread in a manner such that the through-hole conically tapers and narrows as the through-hole extends from the rear side 85a to the front side 85b. The conical through-hole 86 is configured to receive the conical portion 82 of the drive member 80. Moreover, the locking member 85 has, at the front side 85a, radially extending recesses 88 for engagement with a tool for screwing the locking member 85 in and out relative to the tubular portion 44.

In the assembled state, the locking member 85 is within the tubular portion 44 of the first tubular member 40, and the drive member 80 is arranged with the conical portion 82 in the conical through-hole 86 of the locking member 85 while the pinion portion 81 engages the toothed rack at the second tubular member 50. The second tubular member 50 may be inserted into the first tubular member 40 in such a manner that the pinion portion 81 of the drive member 80 is in the uppermost position, i.e., close to a bottom of the inverse U-shaped portion 56. Rotating the drive member 80 by engagement with a tool moves the second tubular member 50 out of the first tubular member 40 to a desired extent. The position of the second tubular member 50 relative to the first tubular member 40 can be locked by screwing the locking member 85 deeper into the tubular portion 44, so that the conical surfaces of the conical portion 82 of the drive member 80 and of the conical through-hole 86 of the locking member 85 engage and lock the drive member 80 by friction, so that the drive member 80 cannot further rotate. The locking can be released by rotating the locking member 85 in the opposite direction.

The third end plate 20' is configured to engage the first end 50a of the second tubular member. As shown in FIGS. 26 to 29, the third end plate 20' is similar to the first end plate 20, and identical or similar parts may be marked with the same reference numerals and the descriptions thereof may not be repeated. The third end plate 20' may have, between the outer surface 20a and the inner surface 20b, through-holes 25 that are arranged at the radially outer end of the webs 23, adjacent to the spikes 27. The through-holes 25 serve for receiving a portion of the teeth 6 of the second tubular member 50, since the webs 53 of the abutment surface 51 of the second tubular member 50 are at the same circumferential position as the teeth 6. At the inner side 20b, a circular step 28 may be formed at a position radially outward from the through-holes 25. The third end plate 20' is attachable to the second tubular member 50 in a manner such that the teeth 6 extend into the through-holes 25.

The second end plate 30 is the same as the second end plate 30 of the first embodiment.

Figure 30:
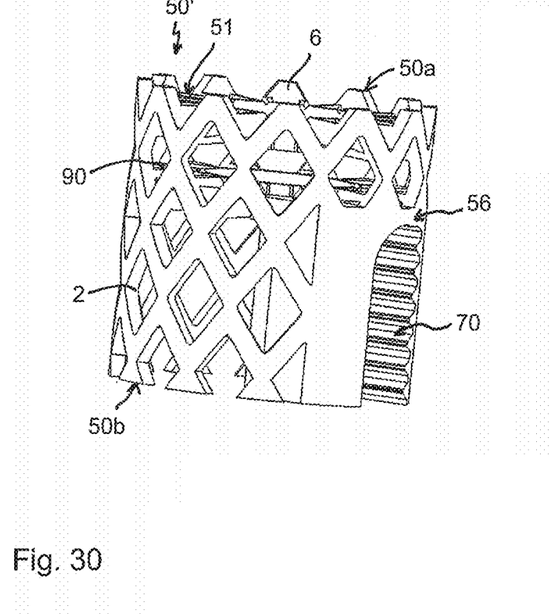
FIG. 30 shows a perspective view of a tubular member of the implant of FIGS. 17 to 19 according to a further embodiment.
Figure 31:
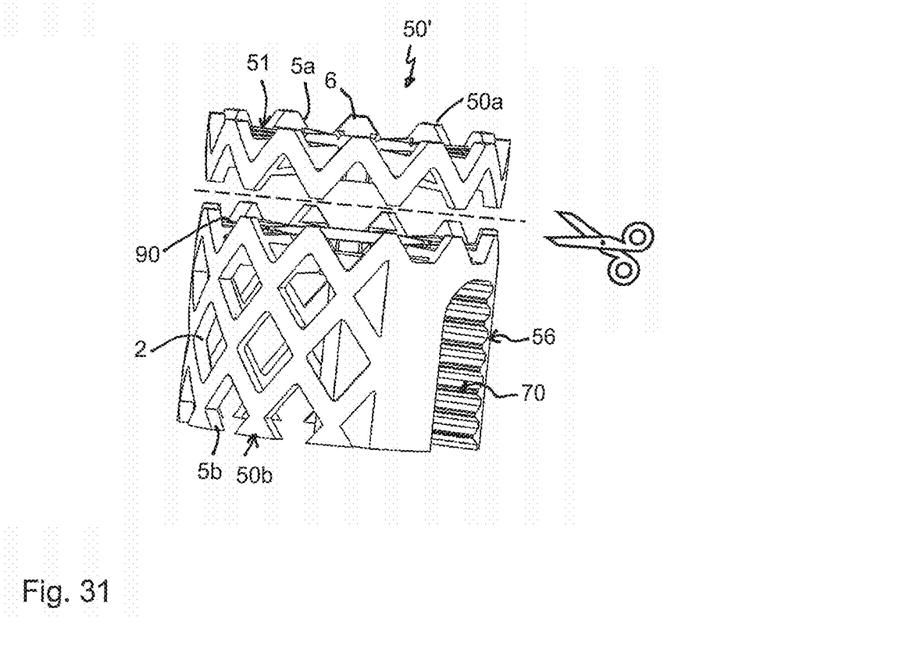
FIG. 31 shows a perspective view of the tubular member of FIG. 30 cut to length.

Referring to FIGS. 30 and 31, in a modification of the second embodiment, the second tubular member 50' can be cut to a desired length. For this arrangement, an intermediate abutment surface 90 is formed at a distance from the first end 50a at a position such when the second tubular member 50' is cut in a plane including the greatest width of the apertures 2, the intermediate abutment surface 90 becomes the first abutment surface, as can be seen in detail in FIG. 31. Hence, a portion of the second tubular member 50' can be cut away as shown, so that the intermediate abutment surface 90 becomes a first abutment surface. If the second tubular member is long enough, several intermediate abutments surfaces 90 may be provided. The second tubular member 50' may be used with the third end plate 20'. If the upper segment is cut away, the teeth 6 of the remaining second tubular member 50' are offset from the teeth 6 before cutting. Hence, as in the first embodiment, the teeth 6 of the intermediate abutment surface 90 can engage the gaps 24 between the webs 23 of the third end plate 20'.

Figure 32:
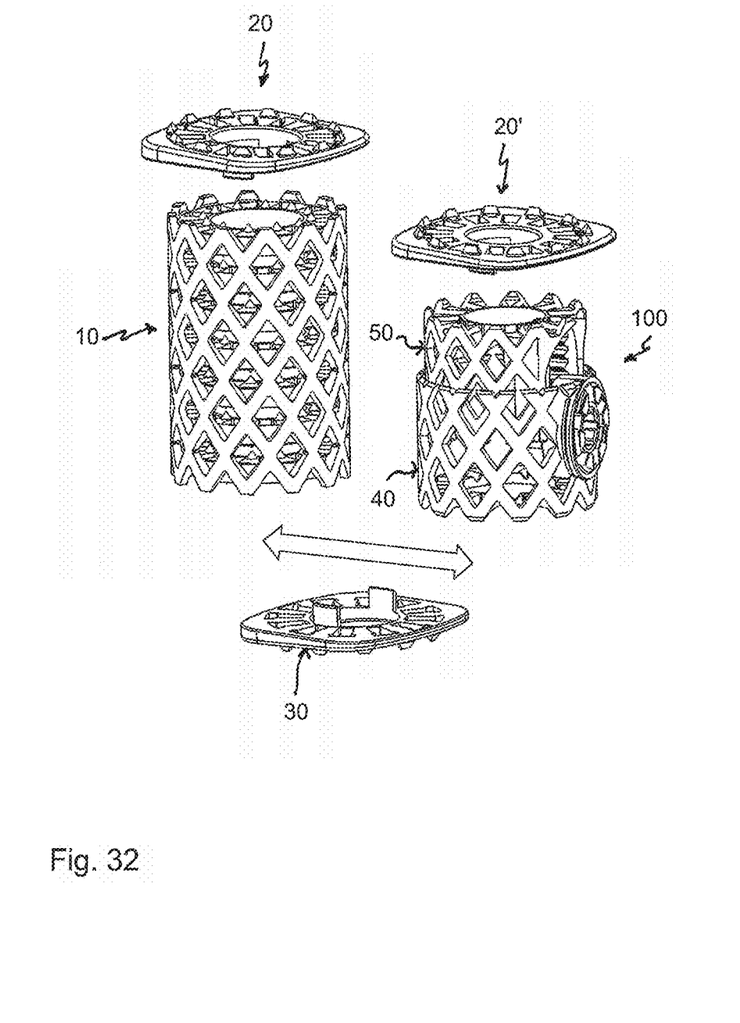
FIG. 32 shows a perspective view of a kit including an implant according to the first embodiment and an implant according to the second embodiment.

FIG. 32 shows a kit of implants and end plates that includes the implant 10 according to the first embodiment and the implant 100 according to the second embodiment that can be used in an interchangeable manner with the same second end plate or bottom end plate 30.

Further modifications of the above described embodiments are also conceivable. For example, the apertures may have a shape other than a diamond shape. The end plates may have another shape, for example, they may have a circular shape, an oval shape, a kidney shape etc. Various other modifications can also be made to the described embodiments without departing from the spirit or scope of the invention.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An implant that is implantable between vertebrae, wherein the implant has a central axis and comprises a monolithic mesh body comprising:

a first end and a second end opposite to the first end, wherein the central axis extends from the first end to the second end, wherein the monolithic mesh body is configured to extend axially over a majority of an entire axial length of the implant, and wherein the monolithic mesh body is configured to be cut to length between the first and second ends;
an inner surface and an outer surface each extending axially from the first end to the second end;
a plurality of teeth at the first end, wherein each of the teeth extends axially away from the second end to a free end; and
a plurality of extensions each extending radially inwardly from the inner surface and spaced apart axially from each other along the central axis between the first and second ends; wherein each extension comprises an abutment surface facing away from the second end that is positioned radially inwardly relative to at least one of the teeth, wherein a first one of the abutment surfaces located at the first end is recessed axially relative to the free ends of the teeth to an extent such that the first abutment surface is configured to contact a vertebra when the implant is implanted.

2. The implant of claim 1, wherein each abutment surface is formed by a plurality of radially extending segments that are spaced apart from each other in a circumferential direction.

3. The implant of claim 1, wherein one of the extensions closest to the second end forms a second abutment surface that faces away from the first end and that is recessed axially relative to the second end to an extent such that the second abutment surface is configured to contact another vertebra when the implant is implanted.

4. The implant of claim 1, wherein a further one of the abutment surfaces is positioned closer axially to the first end than to the second end and is substantially similar to the first abutment surface.

5. The implant of claim 4, wherein the monolithic mesh body is configured to be cut between the first abutment surface and the further abutment surface to separate the first abutment surface from the rest of the implant, such that the further abutment surface is exposed to the outside and configured to contact the vertebra when the implant is implanted.

6. The implant of claim 1, wherein the monolithic mesh body comprises a mesh structure defining a plurality of apertures.

7. The implant of claim 6, wherein at least some of the apertures are open to the first end to at least partially form the plurality of teeth.

8. The implant of claim 6, wherein the apertures are diamond shaped.

9. The implant of claim 1, wherein the shape of the monolithic mesh body is tubular.

10. The implant of claim 1, further comprising an endplate detachably connectable to the first end, wherein the endplate comprises an inner surface configured to engage the first end of the monolithic mesh body and an opposite outer surface configured to engage with the vertebra, and wherein the endplate defines a plurality of apertures configured to receive the teeth when the endplate is connected to the monolithic mesh body.

11. The implant of claim 10, wherein the inner surface of the endplate comprises a plurality of radially extending segments that at least partially define the apertures of the endplate.

12. The implant of claim 1, wherein the monolithic mesh body is formed as a first tubular member, and wherein the implant further comprises a second tubular member that is positionable in and movable axially relative to the first tubular member, and a length adjustment structure for adjusting an axial position of the second tubular member relative to the first tubular member.

13. The implant of claim 12, wherein the length adjustment structure comprises a locking member configured to fix the axial position of the second tubular member relative to the first tubular member.

14. The implant of claim 1, wherein at least one cross-section of the implant, taken perpendicular to the central axis and positioned closer axially to the first end than to the second end but farther from the first end than the abutment surface is to the first end, is devoid of any portions of the implant between the central axis and the inner surface.

15. The implant of claim 1, wherein a portion of the first abutment surface that extends substantially perpendicularly to the central axis is positioned relative to the free ends of the teeth to contact a vertebra when the implant is implanted.

16. A method for implanting an implant between vertebrae, wherein the implant has a central axis and comprises a monolithic mesh body comprising: a first end and a second end opposite to the first end, wherein the central axis extends from the first end to the second end, wherein the monolithic mesh body is configured to extend axially over a majority of an entire axial length of the implant, and wherein the monolithic mesh body is configured to be cut to length between the first and second ends, an inner surface and an outer surface each extending axially from the first end to the second end, a plurality of teeth at the first end, wherein each of the teeth extends axially away from the second end to a free end, and a plurality of extensions each extending radially inwardly from the inner surface and spaced apart axially from each other along the central axis between the first and second ends, wherein each extension comprises an abutment surface facing away from the second end that is positioned radially inwardly relative to at least one of the teeth, the method comprising:
adjusting an axial length of the implant; and
implanting the implant between vertebrae, wherein one of the abutment surfaces located at the first end is recessed axially relative to the free ends of the teeth to an extent such that the one of the abutment surfaces is configured to contact one of the vertebrae.

17. The method of claim 16, wherein the axial length of the implant is adjusted by cutting and separating a portion of the monolithic mesh body at the first end away from the rest of the implant, and wherein after cutting and separating the portion of the monolithic mesh body, the one of the abutment surfaces is located on the rest of the implant.

18. An implant that is implantable between vertebrae, wherein the implant has a central axis and comprises a monolithic mesh body comprising:
a first end and a second end opposite to the first end, wherein the central axis extends from the first end to the second end, and wherein the monolithic mesh body is configured to be cut to length between the first and second ends;
an inner surface and an outer surface each extending axially from the first end to the second end;
a plurality of teeth at the first end, wherein each of the teeth extends axially away from the second end to a free end;
a plurality of extensions spaced apart axially from each other along the central axis between the first and second ends, wherein the plurality of extensions comprises:
a first extension that extends radially inwardly from the inner surface, wherein the first extension has an abutment surface that faces away from the second end and that is recessed axially relative to the free ends of the teeth to an extent such that the abutment surface is configured to contact a vertebra when the implant is implanted;

a second extension that extends radially inwardly from the inner surface and is positioned closer axially to the first end than to the second end, wherein the second extension has an abutment surface that faces away from the second end and that is substantially similar to the abutment surface of the first extension; and at least a third extension that extends radially inwardly from the inner surface and is positioned closer axially to the first end than to the second end, wherein the third extension has an abutment surface that faces away from the second end and that is substantially similar to the abutment surfaces of the first and second extensions.

19. The implant of claim 18, wherein the monolithic mesh body is configured to be cut between the first extension and the second extension to separate the first extension from the rest of the implant, such that the abutment surface of the second extension is exposed to the outside and configured to contact the vertebra when the implant is implanted.

* * * * *